US 7,083,803 B2
Aug. 1, 2006

(12) United States Patent
Peyman

(10) Patent No.: US 7,083,803 B2
(45) Date of Patent: Aug. 1, 2006

(54) OCULAR SOLUTIONS

(75) Inventor: Gholam Peyman, New Orleans, LA (US)

(73) Assignee: Advanced Ocular Systems Limited, Nedlands (AU)

( * ) Notice: Subject to any disclaimer, the term of this patent is extended or adjusted under 35 U.S.C. 154(b) by 39 days.

(21) Appl. No.: 10/752,124

(22) Filed: Jan. 6, 2004

(65) Prior Publication Data
US 2005/0063997 A1 Mar. 24, 2005

Related U.S. Application Data

(63) Continuation-in-part of application No. 10/667,161, filed on Sep. 19, 2003.

(51) Int. Cl.
A61F 13/00 (2006.01)
A61F 2/00 (2006.01)
A61K 9/00 (2006.01)

(52) U.S. Cl. .................. 424/422; 424/400; 424/427; 424/428

(58) Field of Classification Search ............. 424/400, 424/422, 423, 427, 428
See application file for complete search history.

(56) References Cited

U.S. PATENT DOCUMENTS

| 4,079,038 | A | 3/1978 | Choi et al. ................ 260/47 |
| 4,093,709 | A | 6/1978 | Choi et al. ................ 424/19 |
| 4,131,648 | A | 12/1978 | Choi et al. ................ 424/22 |
| 4,138,344 | A | 2/1979 | Choi et al. ................ 252/1 |
| 4,180,646 | A | 12/1979 | Choi et al. ............... 528/153 |
| 4,304,767 | A | 12/1981 | Heller et al. ............... 424/78 |
| 4,946,931 | A | 8/1990 | Heller et al. ............. 528/320 |
| 5,294,604 | A | 3/1994 | Nussenblatt et al. ......... 514/11 |
| 5,387,589 | A | 2/1995 | Kulkarni .................. 514/291 |
| 5,411,952 | A * | 5/1995 | Kaswan |
| 5,457,182 | A | 10/1995 | Wiederrecht et al. ....... 530/402 |
| 5,770,607 | A | 6/1998 | Honbo et al. .............. 514/302 |
| 5,773,019 | A | 6/1998 | Ashton et al. ............. 424/423 |
| 5,952,371 | A | 9/1999 | Baker et al. .............. 514/443 |
| 5,968,543 | A | 10/1999 | Heller et al. ............. 424/425 |
| 6,004,565 | A | 12/1999 | Chiba et al. ............ 424/278.1 |
| 6,179,817 | B1 | 1/2001 | Zhong .................... 604/265 |
| 6,238,799 | B1 | 5/2001 | Opolski .................. 428/423 |
| 6,239,113 | B1 | 5/2001 | Dawson et al. ............. 514/29 |
| 6,258,856 | B1 | 7/2001 | Chamberlain et al. ...... 514/912 |
| 6,306,422 | B1 | 10/2001 | Batich et al. ............. 424/423 |
| 6,331,313 | B1 | 12/2001 | Wong et al. |
| 6,350,442 | B1 | 2/2002 | Garst ................... 424/78.04 |
| 6,413,536 | B1 | 7/2002 | Gibson et al. ............. 424/423 |
| 6,436,906 | B1 | 8/2002 | Or et al. .................. 514/29 |
| 6,440,942 | B1 | 8/2002 | Or et al. .................. 514/29 |
| 6,462,026 | B1 | 10/2002 | Or et al. .................. 514/30 |
| 6,462,071 | B1 | 10/2002 | Castillejos |
| 6,482,799 | B1 * | 11/2002 | Tuse et al. |
| 6,489,335 | B1 * | 12/2002 | Peyman |
| 6,534,693 | B1 | 3/2003 | Fischell et al. |
| 6,596,296 | B1 | 7/2003 | Nelson et al. ............. 424/426 |
| 6,613,355 | B1 | 9/2003 | Ng et al. ................. 424/462 |
| 6,617,345 | B1 | 9/2003 | Gregory et al. ............ 514/395 |
| 6,667,371 | B1 | 12/2003 | Ng et al. ................. 525/462 |
| 6,670,398 | B1 * | 12/2003 | Edwards et al. |
| 6,673,807 | B1 | 1/2004 | Sakai et al. |
| 6,713,081 | B1 | 3/2004 | Robinson et al. |
| 6,864,232 | B1 | 3/2005 | Ueno ....................... 514/9 |
| 6,872,383 | B1 * | 3/2005 | Ueno |
| 2002/0015957 | A1 | 2/2002 | Hageman et al. |
| 2002/0187998 | A1 | 12/2002 | Ueno |
| 2003/0044452 | A1 | 3/2003 | Ueno |
| 2003/0069232 | A1 | 4/2003 | Chiou |
| 2004/0092435 | A1 | 5/2004 | Peyman |
| 2004/0198763 | A1 | 10/2004 | Ueno |
| 2005/0025810 | A1 | 2/2005 | Peyman |
| 2005/0063996 | A1 | 3/2005 | Peyman |
| 2005/0063997 | A1 | 3/2005 | Peyman |
| 2005/0064010 | A1 | 3/2005 | Cooper et al. |
| 2005/0070468 | A1 | 3/2005 | Ueno |

FOREIGN PATENT DOCUMENTS

| CN | 1333018 | 1/2002 |
| CN | 1340358 | 3/2002 |

(Continued)

OTHER PUBLICATIONS

D. Aron-Rosa, *Pulsed Nd:YAG lasers in ophthalmology*, Nd:YAG Laser Applications, pp. 34-48, (1986).

(Continued)

Primary Examiner—Humera N. Sheikh
(74) Attorney, Agent, or Firm—Frommer Lawrence & Haug LLP; Thomas J. Kowalski

(57) ABSTRACT

Ocular solutions containing at least one macrolide antibiotic and/or mycophenolic acid provide anti-inflammatory, anti-cell proliferation, anti-cell migration, anti-angiogenesis, antimicrobial and antifungal effects. In one embodiment, the solution is administered intraocularly after cataract surgery before insertion of a replacement intraocular lens, resulting in reduced posterior capsular opacification which may eliminate the need for a subsequent surgery. The solution may be one that is invasively administered, for example, an irrigation or volume replacement solution containing at least one macrolide antibiotic such as tacrolimus, sirolimus, everolimus, cyclosporine, and ascomycin, or mycophenolic acid. The solution may be one that is non-invasively or topically administered in the form of drops, ointments, gels, creams, etc. and may include eye lubricants and contact lens solutions. The solution may contain a supratherapeutic concentration of agent(s) so that a therapeutic concentration of a topically administered solution accumulates in a diseased ocular structure sufficient to treat the disease.

14 Claims, No Drawings

FOREIGN PATENT DOCUMENTS

| | | |
|---|---|---|
| CN | 1456350 | 11/2003 |
| DE | 19810655 | 9/1999 |
| EP | 1074255 | 2/2001 |
| EP | 1142566 | 10/2001 |
| EP | 0 532 862 | 3/2003 |
| JP | 04010752 | 1/1995 |
| JP | 1997030966 A | 2/1997 |
| JP | 09315954 | 12/1997 |
| JP | 10-218787 | 8/1998 |
| JP | 2001-064198 | 3/2001 |
| WO | WO 89/01772 | 3/1989 |
| WO | WO 99/22722 | 5/1999 |
| WO | WO 99/34830 | 7/1999 |
| WO | WO 99/42104 | 8/1999 |
| WO | WO 00/66122 | 11/2000 |
| WO | WO 02/24234 | 3/2002 |
| WO | WO 02/085928 | 10/2002 |
| WO | WO 03/017990 | 3/2003 |
| WO | WO 03/051385 | 6/2003 |
| WO | WO 2004/014373 | 2/2004 |
| WO | WO2004/027027 | 4/2004 |
| WO | WO 2004/043480 | 5/2004 |
| WO | WO 2004/096261 | 11/2004 |
| WO | WO 2005/011813 | 2/2005 |
| WO | WO2005/027906 | 3/2005 |
| WO | WO 2005/030205 | 4/2005 |

OTHER PUBLICATIONS

Steven H. Dewey, MD, *2003 PCO Update: Part 1—How the square-edged IOL prevenst posterior capsular opacification*, Cataract & Refractive Surgery Today, Sep. 2003, pp. 20-22.

Goodman & Gilman, *The Pharmacological Basis of Therapeutics*, 8th Ed., Pergamon Press, New York, 1990, pp. 1024-1033.

Gholam Peyman, MD, *Pupillary Membranes: Nd:YAG Capsulotomy*, Intravitreal Surgery, Norwalk CT, Appleton & Lange, 1994, pp. 253-257.

Peyman, et al., *Vitreoretinal Surgical Techniques*, Martin Dunitz, London, 2001, Chapter 45, pp. 521-531.

Peyman, U.S. Patent Application Publication, *Treatment of Ocular Disease*, U.S. Appl. No. 10/247,220, filed Sep. 19, 2002, published Jan. 23, 2003.

Schonfield and Kirst, *Macrolide Antibiotics*, Birkhausen, Basil, Switzerland, 2002, pp. 1-36.

Wise, *Handbook of Pharmaceutical Controlled Release Technology*, Marcel Dekker, New York, 2000.

D. Aron-Rosa, *Pulsed Nd: YAG lasers in opthalmology*, Md:YAG Laser Applications, Ed. Buratto, et al., pp. 34-48 (1986).

Algvere et al, *Long-term outcome of RPE allografts in non-immunosuppressed patients with AMD*, European J of Ophthalmology (1999), 9(3):217-230.

Anderson et al, *A Role for Local Inflammation in the Formation of Drusen in the Aging Eye*, American Journal of Opthalmology, vol. 134, No. 3, Sep. 2002, pp. 411-431.

Apel et al, *A subconjunctival degradable implant for cyclosporine delivery in corneal transplant therapy*, Curr. Eye Res. 14:659-667, 1995.

Aramant et al, *Retinal transplantation*, Science & Medicines (2000), 7:20-29.

Carmo et , *Effect of cyclosporin A on the blood-retinal barrier permeability in streptozotocin-induced diabetes*, Mediators of Inflammation (2000), 9(5):243-248.

Cicciarell et al, *Pharmacokinetics of subconjunctivally administered cyclosporine A. Local delivery prior to che-motherapy for retinoblastoma*, IOVS (Mar. 15, 2001), 42(4):S332.

Costantini et al., *Immuophilin Ligands and GDNF Enhance Neurite Branching or Elongation from Developing Dopamine Neurons in Culture*, Experimental Neurology 164:60-70 (2000).

Das et al., *The transplantation of human fetal neuroretinal cells in advanced retinitis pigmentosa patients: Results of a long-term safety study*, Experimental Neurology (1999), 157:58-68.

Del Cerro et al, *Histologic correlation of human neural retinal transplantation*, Invest. Ophthalmology & Visual Science (2000), 41(10):3142-3148.

Donnenfeld et al, *Cyclosporine provides effective treatment for dry eye*, Therapeutic Updates in Ophthalmology, Special Issue, Jul. 1999, pp. 1-3.

Enyedi et al, *Pharmacokinetics and toxicity of an intravitreal device providing sustained release of cyclosporine (CsA) and deaxamethasone (DEX)*, Invest. Ophthalmology and Visual Science, vol. 35, No. 4, 1994, p. 1906, and Annual Meeting of the Association for Research in Vision and Ophthalmology, Sarasota, FL, USA, May 1-6, 1994 abstract.

Enyedi et al, *An intravitreal device providing sustained release of cyclosporine and dexamethasone*, Current Eye Research, May 1996, vol. 15, No. 5, pp. 549-557.

Garweg et a;, *Therapy of Goldmann-Favre's Vitreo-Retinal Degeneration with Cyclosporin A and Bromocriptine*, Klinische Monatsblatter fur Augenheilkunde, vol., 199, No. 3, Sep. 1991, pp. 199-205.

Gilbard, *EW Interview; Electrolyte balance is key to dry-eye product's success*, EyeWorld, Feb. 1999, pp., 20ff.

Grisolano et al., *Retinal Toxicity Study of Intravitreal Cyclosporin*, Opthalmic Surgery, Mar. 1986, 17:155-156.

Jiang, et al, *Corneal electroretinographic function rescued by normal retinal pigment epithelial grafts in retinal degenerative Royal College of Surgeons rats*, Invest. Ophthalmology & Visual Science (1994), 35(13):4300-4308.

Karacorlu et al, *Lack of toxicity of intravitreally administered interferon Alpha-2a*, Ophthalmic Surgery (1999), 23:833-835.

Keep et al., *Introduction: Immunosuppressants as Neuroprotective Agents: Immunosuppressant Analogs in Neuroprotection; Chapter I, Immunosuppressants, Neurologic Disorders, and Neuroprotection*, Ed. Borlongan & Sanberg, Humana Press Inc., Totowa, NJ, pp. 3-32, (Nov. 2002).

Kiryu et al., *In Vivo Evaluation of the Inhibitory Effects of Tacrolimus (FK506) on Leukocyte Accumulation During Retinal Ischemia Reperfusion Injury*, Poster Presentation—1247-B128, (Mar. 1998).

Lai et al, *Local immunosuppresssion prolongs survival of RPE xenografts labeled by retroviral gene transfer*, IOVS (Sep. 2000), 41(10): 3134-3141.

Lailemand et al, *Cyclosporine A delivery to the eye: A pharmaceutical challenge*, European Journal of Pharmaceutics and Biopharmaceutics, 56 (2003), pp. 307-318.

Lipner , *Dry Eye 101: Developing etiologies and treatments for this widespread syndrome* , EyeWorld, Feb. 1999, pp. 19ff.

Lipper et al, *Recent therapeutic advances in dermatology*, JAMA, vol. 283, No. 2, Jan. 12, 2000, pp. 175-177.

Lopez et al, *Transplanted retinal pigment epithelium modifies the retinal degenetation in the RCS*, Invest. Ophthalmology & Visual Science (1989), 30:586-588.

Lund et al, *Subretinal transplantation of genetically modified human cell lines attenuates loss of visual function in dystrophic rats*, PNCS (2001), 98(17):9942-9947.

Martin DF et al., *Synergistic Effect of Rapamycin and Cyclosporin A in the Treatment of Experimental Autoimmune Uveoretinis*, The Journal of Immunology, 1995, 154:922-927.

Nicoletti et al, *The effects of deoxyspergualin on the development of diabetes in diabetes-prone BB rats*, Scandinavian Journal of Immunology (1992), 36(3): 415-420.

Passos et al, *Ocular Toxicity of Intravitreal Tacrolimus*, Ophthalmic Surgery and Lasers, Mar./Apr. 2002, vol. 33, No. 2, pp. 140-144.

PCT, *International Search Report*, PCT/US03/28315, mailed Jun. 15, 2004, 6 pages.

PCT, *International Search Report*, PCT/2004/024054 mailed Jul. 27, 2004, 7 pages.

Peyman et al, *Intravitreal drug therapy*, Japanese Journal of Ophthalmolgy (1989), 33(4):392-404.

Peyman et al, *Keratitis (Noninfectious)*, Principles and Practice of Ophthalmologym W.B. Saunders Company, 1980, pp. 486-449.

Peyman et al, *Implantation of a sustained-release ganciclovir implant*, Vitreoretinal Surgical Techniques, Martin Dunitz Ltd., 2001, Chapter 45, pp., 521-531.

Peyman et al, *Intravitreal Surger: Principles and Practice, 2nd Edition*, 1994, Appleton & Lange, CT, pp. 443-452.

Shen et al, *Combined effect of cyclosporine and sirolimus on improving the longevity of recombinant adenovirus-mediated transgene expression in the retina*, Archives of Ophthalmology (Jul. 2001), 119(7):1033-1043.

Stosic-Grujicic et al, *Leflunomide protects mice from multiple low dose streptozotocin (MLD-SA)-induced insulitis and diabetes*, Clinical & Experimental Immunology (1999), 117(1):44-50.

Ueno, *Use of Macolide Compounds for the Treatment of Dry Eye*, U.S. Patent Application Publication, U.S. Appl. No. 10/354,083, published Jul. 10, 2003, filed Jan. 30, 2003.

Wakelee-Lynch, *Interferon may offer first drug therapy for diabetic retinopathy*, Diabetes Care (1992), 15(2):300-301.

* cited by examiner

OCULAR SOLUTIONS

This application is a Continuation-In-Part of U.S. patent application Ser. No. 10/667,161 filed Sep. 19, 2003, which is expressly incorporated by reference herein in its entirety.

FIELD OF THE INVENTION

The invention is directed to ocular solutions containing macrolide antibiotics to provide anti-inflammatory and other beneficial effects.

BACKGROUND

The eye is naturally bathed internally and externally by ocular fluids. The external portion of the eye is lubricated by lacrimal fluids (tears). The internal portion of the eye has two fluid-containing chambers: the anterior chamber contains the aqueous humor or aqueous, and the posterior chamber contain the vitreous humor or vitreous.

Various conditions require the need to introduce fluids into or on the surface of the eye to replace or replenish naturally occurring fluids. The loss of naturally occurring ocular fluids may be due to normal aging, pathological conditions, surgical intervention, etc. For example, during ocular surgery, the vitreous is frequently removed and must thereafter be replaced. Commercially available irrigating solutions are often used to replace some or all of the vitreous, such as irrigating solutions infused to replace the vitreous removed during vitrectomy and thereby to maintain the shape of the globe. The composition and other properties of these solutions may affect the surgical outcome for the patient, for example, a solution may affect the clarity of the cornea and lens, which may result in decreased visual acuity. Additionally, swelling of the cornea during vitrectomy may be influenced by components of the irrigating solution. Other conditions such as dry eye disease result in decreased external lubrication, and topical solutions such as eye drops are often used to provide relief. Wash solutions are used topically to remove foreign material from the external surface of the eye and invasively to clear the cornea and other structures during surgery.

Ocular solutions, for introduction into the eye and/or topical application, with improved properties are desirable. The invention describes such compositions and method of using the compositions.

SUMMARY OF THE INVENTION

A substitute for an intraocular irrigating, wash, or volume replacement solution is disclosed. The solution contains a concentration in the range from about 1 ng/ml to about 200 µg/ml of a macrolide antibiotic and/or mycophenolic acid. This provides beneficial properties, such as reducing inflammation at a surgical site (anti-inflammatory effect), inhibiting cell migration and cell proliferation (anti-proliferative and anti-migratory effects), inhibiting the growth of new blood vessels at the site of an ocular tumor (anti-angiogenic effect), reducing the growth of bacteria, fungi, etc. (antimicrobial and anti-fungal effects). Its anti-inflammatory effect desirably occurs without an increase in intraocular pressure, which may occur when steroids are administered to control ocular inflammation. Such a composition may be used in patients undergoing ocular surgery such as cataract surgery, retinal repair, etc.

The macrolide and/or mycophenolic acid can be added to a commercially available ocular solution, or can be formulated with an ocular solution. The macrolide antibiotic can be tacrolimus, cyclosporine, sirolimus, everolimus, ascomycin, erythromycin, azithromycin, clarithromycin, clindamycin, lincomycin, dirithromycin, josamycin, spiramycin, diacetyl-midecamycin, tylosin, roxithromycin, ABT-773, telithromycin, leucomycins, and lincosamide. It can be formulated in an inert matrix, a capsule, a liposome, etc. It can be inserted, injected, or implanted within a specific site of the eye (e.g., within the lens capsule), or applied generally to clear or wash a surgical field.

In one embodiment, the inventive ocular composition is administered to a patient undergoing cataract surgery. The solution, containing a concentration in the range from about 20 µg/ml to about 200 µg/ml (about 0.002%$^{w/v}$ to about 0.02%$^{w/v}$) of a macrolide antibiotic and/or mycophenolic acid is introduced within the capsule of the lens after the diseased lens has been removed and before the replacement lens is inserted. Microspheres or microcapsules of the macrolide antibiotic and/or mycophenolic acid can be implanted within the capsule in an alternate embodiment. This can be used to reduce opacification of the posterior capsule, which is a common problem following cataract surgery.

An implantable lens which retains at least one of a macrolide antibiotic or mycophenolic acid is also disclosed. This system provides a replacement lens ready for surgical implantation in a patient undergoing cataract surgery, with the lens containing a concentration of a macrolide antibiotic and/or mycophenolic acid. When the lens is implanted within the lens capsule of a patient's eye, the antibiotic or mycophenolic acid is then released to provide therapeutic effects to the capsule (e.g., anti-cell proliferative effects, anti-inflammatory effects, etc).

In another embodiment, an ocular solution containing a supratherapeutic concentration of a macrolide antibiotic and/or mycophenolic acid is administered topically. The topically administered compounds accumulate within an ocular structure, such as the choroid, retina, or uvea, to a concentration effective to treat ocular pathologies affecting those structures. Such pathologies include diabetic retinopathy, retinitis pigmentosa, age related macular degeneration, scleritis, uveitis, vasculitis, retinoblastoma, choroidal melanoma, pre-malignant and malignant melanoma of the conjunctiva.

In another embodiment, a supratherapeutic concentration of a macrolide antibiotic and/or mycophenolic acid is administered on a contact lens or intraocular device with the agent(s) in an extended release formulation. The agent(s) is formulated to release a maximum intraocular concentration up to about 40 µg/ml.

These and other advantages of the invention will be apparent in light of the following figures and detailed description.

DETAILED DESCRIPTION

An ocular solution containing one or more macrolide antibiotics and/or mycophenolic acid is disclosed. The ocular solution may be any physiologically compatible ocular solution. It may used externally (e.g. topical administration such as on the surface of the conjunctiva) or internally (e.g. invasive administration.)

Ocular solutions are frequently administered to a patient following ocular surgery; macrolide antibiotics in these solutions desirably provide anti-inflammatory effects which aid in post-surgical recovery. In addition, macrolide antibiotics provide these anti-inflammatory effects without an increase in intraocular pressure that often accompanies administration of steroids to post-surgical patients to control inflammation.

Macrolide antibiotics also reduce cell proliferation and cell migration. This may promote the healing process, and may also provide an anti-angiogenesis effect to retard the proliferation and/or growth of new vessels. As one example, controlling the growth of new blood vessels is a way to control proliferation of tumor cells; macrolide antibiotics in an ocular solution may be helpful in controlling ocular neoplasms or tumors. As another example, the solutions may be used in patients having diseases characterized by abnormal angiogenesis, such as certain types of cancers, diabetic retinopathy, and sickle cell retinopathy, in which an anti-angiogenesis effect is desirable. Macrolide antibiotics also provide antimicrobial and antifungal properties to ocular solutions.

Macrolide antibiotics and/or mycophenolic acid may be used to enhance therapy in ocular diseases. Such enhancement is generally defined as treatment of these diseases. Treatment is not limited to total elimination of disease, but is broadly defined to include any enhancement or improvement toward the result of diminishing or alleviating the disease symptoms, onset, course, duration, severity, etc. The inventive use of macrolide antibiotics and/or mycophenolic acid may be combined with other agents, such as chemotherapeutic agents for treatment of ocular malignancies, and cyclooxygenase inhibitors for reducing inflammation. Both acute and chronic ocular diseases are treated by the inventive method and composition, and include retinitis pigmentosa, diabetic retinopathy, age related macular degeneration, scleritis, uveitis, and vasculitis. Ocular cancers such as retinoblastoma, choroidal melanoma, pre-malignant and malignant conjunctival melanoma are also treated by the invention.

It will be appreciated that the inventive composition need not be in the physical form of a true solution, but instead may be a suspension, an emulsion, a gel, etc. It may also encompass the macrolide antibiotic and/or mycophenolic acid in the form of polymeric compositions, microspheres, microvesicles, microcapsules, and/or liposomes. In addition, ocular solutions for topical application may take the form of any of the above, as well as an ointment, a cream, a lotion, etc. Thus, the term solution is used for convenience but encompasses other physical states. It will also be appreciated that the macrolide antibiotics may be included in the formulation for preparing an ocular solution, or may be added in dry form or in concentrated form to an already prepared ocular solution.

The ocular solution may be one that is used as an ocular irrigating solution and/or as a volume replacement solution during ocular surgery. It is thus a substitute for an ocular fluid, such as the vitreous, and/or a substitute for a commercially available irrigating solution that may be used during ocular surgery. It may also be one that is used topically, and thus encompasses eye drops, eye wash solutions, and contact lens solutions. It may be used in over the counter (OTC) ocular solutions for topical application, for example, in ocular solutions such as artificial tears or lubricants. One commercially available ophthalmic lubricant is Viva-Drops®, available from Vision Pharmaceuticals, Inc. (Mitchell S. Dak.). The invention includes but is not limited to this particular embodiment.

In one embodiment, an ocular solution contains at least one macrolide antibiotic and/or mycophenolic acid and is used for intraocular administration. Intraocular administration indicates an invasive route of administration, compared to a topical route of administration. In this embodiment, the ocular solution containing the macrolide antibiotic(s) may be an irrigating solution, a volume replacement solution, and/or a wash solution.

In another embodiment, an ocular solution containing a macrolide antibiotic and/or mycophenolic acid is administered topically, for example, on the conjunctiva or the mucosal surface of the lid, to treat diseases in other areas of the eye, such as the choroid, retina, and uvea. Administration of such compounds was previously restricted to systemic or invasive routes, because it was thought that the higher concentrations of these compounds in internal ocular structures required for efficacy could not be achieved by topical administration. However, an efficacious therapeutic concentration of a topically-administered macrolide antibiotic and/or mycophenolic acid in an ocular structure may be achieved by topically administering a supratherapeutic concentration for a duration such that a therapeutic concentration is attained in the diseased structure.

While not bound by any theory, one reason this therapeutic concentration may be achieved with topical administration is that the structural affinity of the antibiotic and/or mycophenolic acid for lipids results in their accumulation in lipophilic regions of the choroid, retina, etc. Unexpectedly, such topically administered compositions can thus be used to treat pathologies that affect these structures without invasive methods, such as intraocular injection or systemic administration. Examples of pathologies include, but are not limited to, retinopathy including diabetic retinopathy, retinitis pigmentosa, age related macular degeneration, scleritis, uveitis, vasculitis, and oncological diseases affecting the eye such as retinoblastoma, choroidal melanoma, pre-malignant and malignant conjunctival melanoma. Retinoblastoma is a malignant tumor of the retina, typically affecting children under the age of six. Choroidal melanoma is a malignant tumor of the pigmented cells of the choroid. Melanoma of the conjunctiva may be classified as primary acquired melanosis (PAM) with or without atypia, or conjunctival melanoma. For cancers of the eye, treatment with a macrolide antibiotic/mycophenolic acid may provide an anti-angiogenic effect and thereby desirably diminish the blood supply to the tumor. Such treatment may augment or enhance the effects of specific radiation treatments and/or chemotherapeutic agents. For example, the macrolide antibiotic and/or mycophenolic acid may be added in polymer form, providing extended release, to carboplatin, cisplatin, methotrexate, etc., in topical chemotherapy eye drops. Diseases such as diabetic retinopathy, retinitis pigmentosa, and age related macular degeneration are typically chronic so that treatment is prolonged, while diseases such as scleritis, uveitis and vasculitis may be acute with treatment occurring for a shorter duration, that is, over the course of the disease. The invention encompasses both types of treatment, as will subsequently be described.

The topically administered composition must cross ocular structures such as the conjunctiva and sclera to reach structures such as the choroid, retina, and uvea. In transit of the composition, a natural gradient of the active agent(s) may form within the eye. A structure such as the sclera may act as a depot or repository for the active agent(s), providing extended release. Thus, topical administration may provide results similar to a slow release formulation, as will be described. Such formulations desirably decrease the frequency of administration or dosing. For example, patients being treated with the inventive method already have decreased visual acuity, and topical ocular administration of drugs may be difficult and/or uncomfortable for them.

Reducing the frequency of administration enhances compliance, while providing a therapeutic dosage of the composition.

In one embodiment, a concentration of macrolide antibiotic and/or mycophenolic acid in a pharmaceutically acceptable topically administered solution may range from about 0.5%$^{w/v}$ to about 10%$^{w/v}$. In another embodiment, a concentration of macrolide antibiotic and/or mycophenolic acid in a pharmaceutically acceptable topically administered solution may range from about 3%$^{w/v}$ to about 5%$^{w/v}$. In another embodiment, a concentration of macrolide antibiotic and/or mycophenolic acid in a pharmaceutically acceptable topically administered solution may range from about 1%$^{w/v}$ to about 3%$^{w/v}$. In another embodiment, a concentration of macrolide antibiotic and/or mycophenolic acid in a pharmaceutically acceptable topically administered solution may range from about 3%$^{w/v}$ to about 10%$^{w/v}$. In another embodiment, a concentration of macrolide antibiotic and/or mycophenolic acid may range from about 0.1% to about 10% in a topical ocular formulation for treating diabetic retinopathy, age related macular degeneration, or retinitis pigmentosa. In another embodiment, concentrations of macrolide antibiotic and/or mycophenolic acid up to about 2%, up to about 5%, up to about 10%, or exceeding 10% are formulated for topical administration when the compound(s) is bound to a matrix or polymer which slowly releases the compound(s) over time while not exceeding an intraocular concentration of 40 µg/ml, as is subsequently described. In any of the above embodiments, the patient is typically instructed to periodically administer the solution, from once per day up to several times per day, over the course of the disease. In one embodiment, the composition may be administered daily at bedtime. It will be appreciated that some patients with a chronic disease will require continued treatment over many years.

The inventive composition may be used in physiologic ophthalmic irrigating solutions. One example is Balanced Salt Solution (BSS®, available from Alcon Laboratories, Randburg, South Africa), containing per ml 0.64% sodium chloride, 0.075% potassium chloride, 0.048% calcium chloride, 0.03% magnesium chloride, 0.39% sodium acetate, and 0.17% sodium citrate dihydrate, as well as sodium hydroxide and/or hydrochloric acid to adjust pH, and water for injection. Another example is Ocular Irrigation Solution® (Allergan, Irvine Calif.). Another example is lactated Ringer's solution. Another example is a normal saline solution. Another example is normal saline adjusted to pH 7.4 with sodium bicarbonate.

The inventive composition may also be used in ophthalmic volume replacement solutions. For example, it may be introduced into the posterior chamber of the eye to replace the vitreous that is removed during the repair of retinal disorders (vitrectomy).

The inventive composition may also be introduced into the lens capsule during cataract surgery. A cloudy and discolored lens, referred to as a cataract, causes decreased vision and treatment requires that the lens be surgically removed. Cataract surgery usually involves phacoemulsification of the diseased lens inside the capsule, aspiration of the emulsified material, irrigation, and insertion of a replacement intraocular lens (IOL) within the capsule.

Following cataract surgery, there is frequently opacification of the posterior capsule which also diminishes visual acuity. Surgical techniques to minimize posterior capsule opacification have variable success, and patients undergoing cataract surgery may require an additional procedure to attend to the capsular opacification that subsequently occurs.

A complication for IOL implantation is post-operative opacification. This occurs as a result of lens epithelial cells (LEC) which migrate around the posterior capsule, and may be due to lack of maximum contact between the IOL optic and the posterior capsule. In children treated for pediatric cataracts, leaving the posterior capsule intact after IOL implantation predisposes them to secondary cataract formation and severe visual axis opacification (VAO). This usually requires surgery to prevent VAO and an anterior vitrectomy to maintain a clear visual axis during pediatric IOL surgery. Thus, reduction in the extent of cell migration and/or cell proliferation following cataract surgery is desirable.

In this embodiment of the invention, an irrigating or volume replacement solution containing at least one macrolide antibiotic and/or mycophenolic acid is administered to the capsule with or before inserting the replacement lens. Without being bound by any theory, the macrolide antibiotic and/or mycophenolic acid may reduce posterior capsular opacification and visual axis opacification by its inhibitory effect on ocular cell proliferation and cell migration.

The macrolide antibiotic and/or mycophenolic acid can also be provided on a device, such as a contact lens applied to the exterior surface of an eye, or a lens that will be implanted within a patient's eye. Implantable lenses include any IOL used to replace a patient's diseased lens following cataract surgery, including but not limited to those manufactured by Bausch and Lomb (Rochester N.Y.), Alcon (Fort Worth Tex.), Allergan (Irvine Calif.), and Advanced Medical Optics (Santa Ana Calif.). The system provides a therapeutic replacement lens ready for surgical implantation in a patient. When the lens is implanted within the lens capsule, the antibiotic and/or mycophenolic acid provides therapeutic effects (e.g., anti-cell proliferative effects, anti-inflammatory effects, etc) to the eye.

A concentration of the macrolide antibiotic and/or mycophenolic acid within the capsule is provided to achieve the previously described therapeutic effect. In one embodiment, the concentration ranges from about 20 µg/ml (about 0.002%$^{w/v}$) to about 2000 µg/ml (about 0.2%$^{w/v}$). In another embodiment, the concentration ranges from about 200 µg/ml (about 0.02%$^{w/v}$) to about 2000 µg/ml (about 0.2%$^{w/v}$). In another embodiment, the concentration ranges from about 20 µg/ml (about 0.002%$^{w/v}$) to about 200 µg/ml (about 0.02%$^{w/v}$).

In another embodiment, the IOL or device contains a concentration of the macrolide antibiotic and/or mycophenolic acid up to about 2%$^{w/v}$ formulated so that the concentration in the eye at any time does not exceed about 40 µg/ml. For example, the intraocular concentration of the active agent(s) at any time may be in the range of about 10 µg/ml to about 30 µg/ml. Such formulation methods are known to one skilled in the art and include, but are not limited to, extended release formulations subsequently described.

The contact lens or IOL may be made of hydrophobic or hydrophilic material. The type of material determines whether the lens cannot fold, is rigid and requires a large incision to insert, or is flexible to allow the lens to be rolled, compressed, or folded for insertion through a smaller incision. The most common materials used in lenses are various chemical modifications of silicon, hydrophobic acrylates, hydrophobic acrylates, and hydrogels which contain water to impart gel-like characteristic to the material. Each of these can be formulated or treated to contain a solution containing a macrolide antibiotic and/or mycophenolic acid.

In one embodiment, the contact lens or implantable IOL is packaged in an ophthalmically acceptable medium which contains the macrolide antibiotic and/or mycophenolic acid. For example, a porous hydrogel lens (e.g., Hydroview®, Bausch & Lomb Surgical, Rochester N.Y.) retains the macrolide antibiotic and/or mycophenolic acid within the pores. Upon application of the contact lens or insertion/implantation of the lens into the lens capsule, the macrolide antibiotic and/or mycophenolic acid is released. An ocular device containing agent(s) in a slow-release system provides extended therapy, for example, over a post-surgical recovery period as the actives are slowly released through the porous elements. It may also be the administration method of choice in some patients, such as patients who are elderly, who cannot reliably self-administer topical ocular medications, who must receive chronic therapy, etc.

In another embodiment, a contact lens or implantable lens is coated to provide the macrolide antibiotic and/or mycophenolic acid. This embodiment may be used with a non-hydrogel hydrophilic lens, a hydrophobic lens, a lens made from an acrylic material (e.g., AcrySof®; Alcon, Fort Worth Tex.; Sensar®; Advanced Medical Optics, Santa Ana Calif.), a silicone lens (e.g., CeeOn®, Pharmacia & Upjohn Company, Pickering Ohio.), etc. Coating and/or incorporation procedures that may be used are known to one skilled in the art; for example, as disclosed in U.S. Pat. Nos. 6,238,799; 6,179,817; 6,306,422; and 6,258,856, each of which is incorporated by reference herein in its entirety. The macrolide antibiotic and/or mycophenolic acid may be added to the storage solution during packaging of the lens, or may be incorporated into the manufacture of the lens. For example, the macrolide antibiotic and/or mycophenolic acid may be incorporated into either or both the hydration fluid in the formation of a hydrophilic or hydrogel lens, or in the storage solution. In another example, the macrolide antibiotic and/or mycophenolic acid may be in an acceptable encapsulated form in a hydrogel IOL for extended long term release.

The inventive composition may also be used as an ocular wash solution, for example, to clear the surgical field during intraocular surgery.

In each of the above embodiments, any macrolide antibiotic alone or in combination may be used. Embodiments of the invention include various ocular-compatible concentrations of the macrolide antibiotic(s) and/or mycophenolic acid sufficient to provide an anti-inflammatory, anti-proliferative, anti-cell migration, anti-fungal, etc. effect. Concentrations may depend upon the use for the composition, as is known to one skilled in the art. Thus, in these embodiments, the invention is not limited to a specific concentration of macrolide antibiotic and/or mycophenolic acid. In general, the macrolide antibiotic and/or mycophenolic acid is present in the ocular solution at concentrations ranging from about 1 ng/ml (about $0.0000001\%^{w/v}$) to about 200 µg/ml (about $0.02\%^{w/v}$). In one embodiment, the macrolide antibiotic and/or mycophenolic acid is present in the ocular solution at a concentration of about 1 µg/ml (about $0.0001\%^{w/v}$). For use to reduce capsular opacification following cataract surgery, concentrations ranging from about 1 µg/ml (about $0.0001\%^{w/v}$) to about 200g/ml (about $0.02\%^{w/v}$), or from about 20 µg/ml (about $0.002\%^{w/v}$) to about 200 µg/ml (about $0.02\%^{w/v}$), may be used. The properties of the macrolide- and/or mycophenolic acid-containing ocular solution are compatible with ocular tissues.

The macrolide antibiotic and/or mycophenolic acid may be formulated with a viscoelastic substance such as hyaluranic acid, or may be contained in microspheres, macrospheres, microvesicles, macrovesicles, microcapsules, macrocapsules, liposomes, etc., as described in co-pending U.S. patent application Ser. No. 10/631,143 which is expressly incorporated by reference herein in its entirety. This embodiment may be used with solutions administered to prevent capsular opacification following cataract surgery, as previously described.

Liposomes may be prepared from dipalmitoyl phosphatidylcholine (DPPC), for example, from egg phosphatidylcholine (PC), a lipid with a low heat of transition. Liposomes are made using standard procedures as known to one skilled in the art. The macrolide antibiotic(s), in amounts ranging from nanogram to microgram quantities, or higher, is added to a solution of egg PC, and the lipophilic drug binds to the liposome.

A time-release drug delivery system may be administered intraocularly to result in sustained release of the macrolide antibiotic(s) over a period of time. The formulation may be in the form of a vehicle, such as a micro- or macro-capsule or matrix of biocompatible polymers such as polycaprolactone, polyglycolic acid, polylactic acid, polyanhydrides, polylactide-co-glycolides, polyamino acids, polyethylene oxide, acrylic terminated polyethylene oxide, polyamides, polyethylenes, polyacrylonitriles, polyphosphazenes, poly (ortho esters), sucrose acetate isobutyrate (SAIB), and other polymers such as those disclosed in U.S. Pat. Nos. 6,667, 371; 6,613,355; 6,596,296; 6,413,536; 5,968,543; 4,079, 038; 4,093,709; 4,131,648; 4,138,344; 4,180,646; 4,304, 767; 4,946,931, each of which is expressly incorporated by reference herein in its entirety, or lipids that may be formulated as microspheres or liposomes. A microscopic or macroscopic formulation may be administered through a needle, or may be implanted by suturing within the eye, for example, within the lens capsule. As an illustrative example, sirolimus may be mixed with polyvinyl alcohol (PVA), the mixture then dried and coated with ethylene vinyl acetate, then cooled again with PVA. In a formulation for intraocular administration, the liposome capsule degrades due to cellular digestion providing a slow release drug delivery system, allowing the patient a constant exposure to the drug over time.

A time-release microscopic or macroscopic formulation may also be topically administered. The sustained-release antibiotic(s) and/or mycophenolic acid accumulates at concentrations in ocular structures such as the choroid or retina sufficient to effect treatment and diseases affecting these structures.

Delayed or extended release properties may be provided through various formulations of the vehicle (coated or uncoated microsphere, coated or uncoated capsule, lipid or polymer components, unilamellar or multilamellar structure, and combinations of the above, etc.). Other variables may include the patient's pharmacokinetic-pharmacodynamic parameters (e.g., body mass, gender, plasma clearance rate, hepatic function, etc.). The formulation and loading of microspheres, microcapsules, liposomes, etc. and their ocular implantation are standard techniques known by one skilled in the art, for example, the use a ganciclovir sustained-release implant to treat cytomegalovirus retinitis, disclosed in Vitreoretinal Surgical Techniques, Peyman et al., Eds. (Martin Dunitz, London 2001, chapter 45); Handbook of Pharmaceutical Controlled Release Technology, Wise, Ed. (Marcel Dekker, New York 2000), the relevant sections of which are incorporated by reference herein in their entirety.

Examples of macrolide antibiotics that may be used for intraocular administration include, but are not limited to, tacrolimus, Cyclosporin A, sirolimus, ascomycin, and everolimus. Tacrolimus (Prograf®, Fujisawa Healthcare, Deerfield, Ill.; FK-506), a macrolide immunosuppressant produced by *Streptomyces tsukubaensis*, is a tricyclo hydrophobic compound that is practically insoluble in water, but is freely soluble in ethanol and is very soluble in methanol and chloroform. It is available under prescription as either capsules for oral administration or as a sterile solution for intravenous administration. The solution contains the equivalent of 5 mg anhydrous tacrolimus in 1 ml of polyoxyl 60 hydrogenated castor oil (HCO-60), 200 mg, and dehydrated alcohol (USP, 80.0%$^{w/v}$), and must be diluted with a solution of 0.9% NaCl or 5% dextrose before use.

Tacrolimus has been used for topical administration to treat a variety of dermatoses. Topical administration of tacrolimus at doses ranging from 0.03%–0.3% resulted in significant clinical improvement in atopic dermatitis after 2–3 weeks treatment, and tacrolimus treatment of other dermatologic diseases shows promise. Tacrolimus, like cyclosporine, blocks the signal transduction pathway needed to induce interleukin-2 gene expression and thereby activate T lymphocytes. In addition to suppressing T cell activation, tacrolimus inhibits anti-lgE-triggered histamine release and inhibits prostaglandin D2 synthesis in human skin mast cells. While oral administration produces limiting adverse effects (systemic immunosuppression, infection, neural toxicity, nephrotoxicity, and hypertension), topical administration for treatment of dermatoses at concentrations up to 0.3% showed no significant difference in effects between treated and control groups. In addition, tacrolimus is well tolerated locally and only occasionally causes mild irritation.

The use of tacrolimus as a specific medicament for treatment of ocular disease has been disclosed in U.S. Pat. No. 6,489,335 and co-pending U.S. patent application Ser. No. 10/247,220, each of which is expressly incorporated by reference herein in its entirety. For example, tacrolimus may be contained in an aqueous-based cream excipient for topical application, or it may be injected intraocularly, or it may be administered surgically as an ocular implant.

None of these publications disclose the topical ocular administration of supratherapeutic concentrations of a macrolide antibiotic and/or mycophenolic acid, either alone or with other agents such as chemotherapeutic agents and/or inhibitors of cyclooxygenase, at the disclosed doses and formulations for treating ocular pathologies such as diabetic retinopathy, retinitis pigmentosa, age related macular degeneration, uveitis, vasculitis, retinoblastoma, choroidal melanoma, pre-malignant and malignant melanoma of the conjunctiva, as in the inventive method.

Cyclosporin A (cyclosporine, topical formulation Arrestase®, Allergan Inc.) is a cyclic peptide produced by *Trichoderma polysporum*. It is available commercially, for example, from Sigma-Aldrich (St. Louis Mo.). It is an immunosuppressant and acts in a particular subset of T lymphocytes, the helper T cells. Cyclosporin A exerts an immunosuppressant effect by inhibiting production of the cytokine interleukin 2. Each of Cyclosporin A and tacrolimus, another immunosuppressant, produce significant renal and hepatic toxicity when each is administered systemically; because of this toxicity, they are not administered together.

Cyclosporin A has been administered to treat ocular conditions such as glaucoma, corticosteroid-induced ocular hypertension, allograft rejection, infections, and ocular surface disease. Its use has been reported for the treatment of uveitis (inflammation of the uvea) by topical, intravitreal or systemic administration with doses of 0.05%, 0.1%, and 0.5%. Cyclosporin A has good penetration into the cornea but not into the anterior chamber, and does not increase intraocular pressure or cause cataracts. Its known toxicity had previously limited its use for other ocular diseases.

The use of Cyclosporin A as a specific medicament for treatment of ocular disease with reduced toxicity has been described in co-pending U.S. patent application Ser. No. 10/289,772, which is expressly incorporated by reference herein in its entirety.

Sirolimus, also known as rapamycin, RAPA, and Rapamune®, is a triene macrolide antibiotic derived from *Streptomyces hydroscopicus* and originally developed as an antifungal agent. Subsequently, it has shown anti-inflammatory, anti-tumor, and immunosuppressive properties. Ascomycin, also known as pimecrolimus, Immunomycin, and FR-900520, is an ethyl analog of tacrolimus and has strong immunosuppressant properties. It inhibits Th1 and Th2 cytokines, and preferentially inhibits activation of mast cells, and is used to treat contact dermatitis and other dermatological conditions. Sirolimus and ascomycin are commercially available, e.g., A.G. Scientific, Inc. (San Diego, Calif.).

Regarding its immunosuppressive potential, sirolimus has some synergetic effect with Cyclosporin A. It has been reported that sirolimus has a different mode of action compared to Cyclosporin A and tacrolimus. All three agents are immunosuppressants which affect the action of immune cell modulators (cytokines), but do not affect the immune cells themselves. However, while all three agents affect immune cell modulators, they do so differently: Cyclosporin A and tacrolimus prevent synthesis of cytokine messengers, specifically interleukin-2, while sirolimus acts on cytokine that has already been synthesized, preventing it from reaching immune cells.

Sirolimus inhibits inflammation by acting on both T-lymphocytes and dendritic cells. The latter are the first cells to recognize antigens. Sirolimus blocks the growth of dendritic cells and a number of other cells, such as tumors and endothelial cells, which are activated by the tumor cell releasing vascular endothelial growth factor (VEGF). VEGF is a central regulator of angiogenesis (formation of new blood vessels from pre-existing vessels) and vasculogenesis (development of embryonic vasculature through an influence on endothelial cell differentiation and organization). Diseases that are characterized by abnormal angiogenesis and vasculogenesis, such as some cancers and some ocular diseases, may show abnormal production of VEGF. Thus, control of VEGF function may be one means to control or treat these diseases. Sirolimus has also been used in the prevention of smooth muscle hyperplasia after coronary stent surgery. The use of sirolimus and ascomycin as specific medicaments for treatment of ocular disease has been disclosed in co-pending U.S. patent application Ser. No. 10/631,143, which is expressly incorporated by reference herein in its entirety.

Everolimus, also known as RAD-001, SCZ RAD, Certican™ (Novartis, Basel Switzerland), is an analog of sirolimus but is a new and distinct chemical entity. It is an oral immunosuppressant that inhibits growth factor-induced cell proliferation and thus reduces acute organ rejection and vasculopathy, the proliferation of smooth muscle cells in the innermost wall of grafts that restricts blood supply.

Mycophenolic acid (MPA) is the active compound formed following the administration of mycophenolate mofetil (MMF). The prodrug is the morpholinoethyl ester of mycophenolic acid. Mycophenolic acid is an antileukemic and immunosuppressant agent used in patients undergoing chemotherapy for cancer and in transplant recipients.

The topical ocular administration of these agents, either alone, in combination, or with chemotherapeutic agents or cyclooxygenase inhibitors, at the disclosed concentrations and formulations to treat ocular pathologies such as diabetic retinopathy, retinitis pigmentosa, age related macular degeneration, uveitis, vasculitis, retinoblastoma, choroidal melanoma, pre-malignant and malignant conjunctival melanoma has not been reported.

The addition of these agents, either alone or in combination, to invasively administered ocular solutions according to the invention provides beneficial anti-inflammatory, anti-proliferative, anti-cell migration, anti-angiogenic, antimicrobial, and antifungal properties.

It will be appreciated that the invention encompasses the use of macrolide antibiotics and/or mycophenolic acid, in addition to those previously described, in an ocular solution. These include, for example, the known antibiotics erythromycin and its derivatives such as azithromycin and clarithromycin, lincomycin, dirithromycin, josamycin, spiramycin, diacetyl-midecamycin, troleandomycin, tylosin, and roxithromycin. The invention also includes new macrolide antibiotic scaffolds and derivatives in development, including but not limited to the ketolides ABT-773 and telithromycin as described by Schonfeld and Kirst (Eds.) in Macrolide Antibiotics, Birkhauser, Basel Switzerland (2002); macrolides derived from leucomycins, as described in U.S. Pat. Nos. 6,436,906; 6,440,942; and 6,462,026 assigned to Enanta Pharmaceuticals (Watertown Mass.); and lincosamides.

In addition to the above described uses, the invention comprises ocular solutions for topical (non-invasive) ocular administration with everolimus, erythromycin, azithromycin, clarithromycin, lincomycin, dirithromycin, josamycin, spiramycin, diacetyl-midecamycin, tylosin, roxithromycin, and mycophenolic acid, as well as the previously described new macrolide antibiotic scaffolds and derivatives in development, including but not limited to the ketolides ABT-773 and telithromycin, macrolides derived from leucomycins, and lincosamides.

The macrolide antibiotics are included with ocular solutions for any use. They may be included with topical ocular solutions containing chemotherapeutic agents for treating ocular malignancies or pre-malignant conditions. They may be included with topical ocular solutions containing inhibitors of cyclooxygenase for reducing ocular inflammation. In one embodiment, age related macular degeneration is treated by administering a topical ocular formulation containing at least one macrolide antibiotic and/or mycophenolic acid and at least on cyclooxygenase inhibitor. The cyclooxygenase inhibitor(s) may be present in a concentration of 0.5% to 20% of the composition. Inhibitors of cyclooxygenase (COX inhibitors) are well known (e.g., "Vioxx®", "Mereck, Whitehouse Station, N.J." Celebrex®, "Pfizer, Groten Conn.") and include, but are not limited to, ibuprofen, indomethacin, piroxicam, and tranylcypromine HCl. The macrolide antibiotic may be added together or separately as individual components in the preparation of an ocular solution. Alternatively, a solution of the macrolide antibiotic may be prepared and then added to the ocular solution. The solutions may be commercial irrigating solutions that contain other known components, such as various anions and cations, buffers to regulate pH, adenosine, calcium, glucose, bicarbonate, dextrose, dextran 40 (a low molecular weight colloidal osmotic agent), gentamicin, dexamethasone, selenium, zinc, and gluconide. The macrolide antibiotic may be added to commercial ocular lubricating solutions, such as artificial tears. The macrolide antibiotic may be included with commercial ocular wash solutions. The macrolide antibiotic may be included with contact lens wash, rinse, and wetting solutions. Any solution for ocular administration, either administration to the exterior surface of the eye or to one of the interior chambers of the eye, may contain the macrolide antibiotic.

The invention is also not limited to human use, and encompasses the use of ocular solutions containing at least one macrolide antibiotic for veterinary use. For example, lincosamides have been used in animals; an ocular solution containing a lincosamide may be used as a veterinary irrigation solution, volume replacement solution, topical wash or lubricant solution, etc.

The invention provides general purpose ocular solutions in the form of eye drops, eye washes, eye irrigating solutions, volume replacement solutions, contact lens solutions, etc. that contain one or more of the above macrolide antibiotics. In various embodiments, the ocular solution may be in single or multi-dose containers (e.g., 10 ml, 20 ml, 30 ml, 500 ml).

Other variations or embodiments of the invention will also be apparent to one of ordinary skill in the art from the above figures and descriptions. Thus, the forgoing embodiments are not to be construed as limiting the scope of this invention.

What is claimed is:

1. A method to treat a posterior segment disease affecting at least one of a choroid, retina, uvea, or lens capsule in a patient's eye comprising administering to the eye of a patient with retinopathy, retinitis pigmentosa, or age related macular degeneration a composition in an extended release formulation on a contact or intraocular lens, the composition comprising a concentration ranging between $0.5\%^{w/w}$ to about $10\%^{w/w}$ of a macrolide antibiotic and/or mycophenolic acid in a pharmaceutically acceptable topical formulation for a duration to achieve a concentration of the macrolide antibiotic and/or mycophenolic acid in a diseased posterior segment ocular structure sufficient to treat the affected choroid, retina, uvea, or lens capsule.

2. The method of claim 1 wherein the macrolide antibiotic is selected from the group consisting of tacrolimus, Cyclosporin A, sirolimus, ascomycin, and everolimus.

3. The method of claim 1 wherein the macrolide antibiotic is selected from the group consisting of erythromycin, azithromycin, clarithromycin, lincomycin, dirithromycin, josamycin, spiramycin, diacetyl-midecamycin, tylosin, troleandomycin, roxithromycin, ABT-773, telithromycin, macrolides derived from leucomycins, and lincosamides.

4. The method of claim 1 wherein the composition is formulated as at least one selecting from the group consisting of a polymer, a microcapsule, a microsphere, a microvesicle, and a liposome.

5. The method of claim 1 for administration to at least one of an ocular mucosal surface or the conjunctiva.

6. The method of claim 1 wherein the concentration of the macrolide antibiotic and/or mycophenolic acid is from at least one of about $0.5\%^{w/v}$ to about $3\%^{w/v}$, about $3\%^{w/v}$ to about $5\%^{w/v}$, about $5\%^{w/v}$, to about $10\%^{w/v}$, or about $3\%^{w/v}$ to about $0.5\%^{w/v}$.

7. The method of claim 1 for treating age related macular degeneration wherein the composition further comprises a cyclooxygenase inhibitor.

8. A method to treat a posterior segment disease affecting at least one of a choroid, retina, uvea, or lens capsule in a patient's eye comprising administering to the eye of a patient with retinopathy, retinitis pigmentosa, or age related macular degeneration a composition in an extended release formulation on a contact or intraocular lens, the composition consisting essentially of tacrolimus at a concentration from $0.5\%^{w/v}$ to about $10\%^{w/v}$ in a pharmaceutically acceptable formulation for a duration to achieve a concentration in an internal ocular structure sufficient to treat the affected choroid, retina, uvea, or lens capsule.

9. A method to treat a posterior segment disease affecting at least one of a choroid, retina, uvea, or lens capsule in a patient's eye comprising administering to the eye of a patient with retinopathy, retinitis pigmentosa, or age related macular degeneration a composition in an extended release formulation on a contact or intraocular lens, the composition consisting essentially of Cyclosporin A at a concentration from $0.5\%^{w/v}$ to about $10\%^{w/v}$ in a pharmaceutically acceptable formulation for a duration to achieve a concentration in an internal ocular structure sufficient to treat the affected choroid, retina, uvea, or lens capsule.

10. A method to treat a posterior segment disease affecting at least one of a choroid, retina, uvea, or lens capsule in a patient's eye comprising administering to the eye of a patient with retinopathy, retinitis pigmentosa, or age related macular degeneration a composition in an extended release formulation on a contact or intraocular lens, the composition consisting essentially of sirolimus at a concentration from $0.5\%^{w/v}$ to about $10\%^{w/v}$ in a pharmaceutically acceptable formulation for a duration to achieve a concentration in an internal ocular structure sufficient to treat the affected choroid, retina, uvea, or lens capsule.

11. A method to treat a posterior segment disease affecting at least one of a choroid, retina, uvea, or lens capsule in a patient's eye comprising administering to the eye of a patient with retinopathy, retinitis pigmentosa, or age related macular degeneration a composition in an extended release formulation on a contact or intraocular lens, the composition consisting essentially of ascomycin at a concentration from $0.5\%^{w/v}$ to about $10\%^{w/v}$ in a pharmaceutically acceptable formulation for a duration to achieve a concentration in an internal ocular structure sufficient to treat the affected choroid, retina, uvea, or lens capsule.

12. A method to treat a posterior segment disease affecting at least one of a choroid, retina, uvea, or lens capsule in a patient's eye comprising administering to the eye of a patient with retinopathy, retinitis pigmentosa, or age related macular degeneration a composition in an extended release formulation on a contact or intraocular lens, the composition consisting essentially of everolimus at a concentration from $0.5\%^{w/v}$ to about $10\%^{w/v}$ in a pharmaceutically acceptable formulation for a duration to achieve a concentration in an internal ocular structure sufficient to treat the affected choroid, retina, uvea, or lens capsule.

13. A method to treat a posterior segment disease affecting at least one of a choroid, retina, uvea, or lens capsule of an eye in a patient having diabetic retinopathy, age related macular degeneration, or retinitis pigmentosa, the method comprising administering to the eye a composition comprising a concentration ranging between $0.1\%^{w/w}$ to about $10\%^{w/w}$ of a macrolide and/or mycophenolic acid in a pharmaceutically acceptable topical formulation for a duration to achieve a concentration of the macrolide antibiotic and/or mycophenolic in a diseased posterior segment ocular structure sufficient to treat the affected choroid, retina, uvea, or lens capsule.

14. The method of claim 13 wherein the composition further comprises at least one cyclooxygenase inhibitor.

* * * * *

UNITED STATES PATENT AND TRADEMARK OFFICE
CERTIFICATE OF CORRECTION

PATENT NO. : 7,083,803 B2  Page 1 of 1
APPLICATION NO. : 10/752124
DATED : August 1, 2006
INVENTOR(S) : Gholam Peyman It is certified that error appears in the above-identified patent and that said Letters Patent is hereby corrected as shown below:

In The Claims:

Column 12, Claim 4, line 50    "selecting" should be --selected--;

Column 12, Claim 6, line 58    delete "," after second occurrence of "$5\%^{w/v}$";

Column 12, Claim 6, line 59    "0.5%" should be --10%--;

Column 14, Claim 13, line 26   remove "antibiotic" after "macrolide"

Signed and Sealed this

Fifth Day of December, 2006

JON W. DUDAS
*Director of the United States Patent and Trademark Office*

UNITED STATES PATENT AND TRADEMARK OFFICE
CERTIFICATE OF CORRECTION

PATENT NO. : 7,083,803 B2  Page 1 of 1
APPLICATION NO. : 10/752124
DATED : August 1, 2006
INVENTOR(S) : Gholam Peyman It is certified that error appears in the above-identified patent and that said Letters Patent is hereby corrected as shown below:

In The Claims:

Column 12, Claim 1, line 30     Replace "pigimentosa" after "retinitis" with
--pigmentosa--

Signed and Sealed this

Ninth Day of January, 2007

JON W. DUDAS
*Director of the United States Patent and Trademark Office*